United States Patent [19]

Jacobs et al.

[11] Patent Number: 5,593,978
[45] Date of Patent: Jan. 14, 1997

[54] GROWTH PROMOTING COMPOSITION FOR FISH AND METHOD OF USING THE SAME

[75] Inventors: Martin J. Jacobs, Terre Haute, Ind.; Fred J. Hart, Glen Alpine, Australia

[73] Assignee: Mallinckrodt Veterinary, Inc., Mundelein, Ill.

[21] Appl. No.: 166,870

[22] Filed: Dec. 15, 1993

[51] Int. Cl.$^6$ .................. A61K 31/715; C07D 313/08
[52] U.S. Cl. .................. 514/58; 514/450; 549/270; 426/2; 426/271; 426/805
[58] Field of Search .................. 426/2, 271, 805; 514/58, 450; 549/270

[56] References Cited

U.S. PATENT DOCUMENTS

| | | |
|---|---|---|
| 3,196,019 | 7/1965 | Andrews et al. |
| 3,239,341 | 3/1966 | Hodge et al. |
| 3,329,345 | 3/1966 | Hodge et al. |
| 3,329,348 | 3/1966 | Hodge et al. |
| 3,331,356 | 7/1967 | Eckstein. |
| 3,574,235 | 4/1971 | Young. |
| 3,687,982 | 8/1972 | Young. |
| 3,751,431 | 8/1973 | Wehrmeister et al. |
| 3,903,304 | 9/1975 | Groninger et al. |
| 4,210,634 | 7/1980 | Jaeger. |
| 4,778,821 | 10/1988 | Clough et al. .................. 514/450 |
| 4,843,064 | 6/1989 | Vaughan et al. |
| 5,030,657 | 7/1991 | Burtle et al. |
| 5,229,146 | 7/1993 | Tanaka .................. 426/1 |

FOREIGN PATENT DOCUMENTS

| | | |
|---|---|---|
| 0272976 | 6/1988 | European Pat. Off. |
| 0299794 | 1/1989 | European Pat. Off. |
| 8503440 | 8/1985 | WIPO. |

OTHER PUBLICATIONS

Zeranol and Dietary Protein Level Effects On Live Performance, Carcass Merit, Certain Endocrine Factors And Blood Metabolite Levels Of Steers, M. L. Borger, L. L. Wilson, J. D. Sink, J. H. Ziegler and S. L. Davis, Journal of Animal Science, vol. 36, No. 4, 1973, pp. 706–711.

Effects of Breed and Zeranol Implantation On Serum Insulin, Somatomedin–Like Activity And Fibroblast Proliferative Activity, P. J. Wangsness, R. F. Olsen, and R. J. Martin, Journal of Animal Science, vol. 52, No. 1, 1981, pp. 57–62.

Liveweight Gains, Blood Levels Of Metabolites, Proteins and Hormones Following Implantation Of Anabolic Agents In Steers, R. J. Heitzman, K. H. Chan and I. C. Hart, British Veterinary Journal, vol. 133 (1977), pp. 62–70.

Growth Promotion and Feeding, Hormones and Aquaculture, Fish, Endocrinology, A. J. Matty (1985) pp. 234–241.

Hormonal Growth Promotion and Evidence for a Size–Related Difference in Response to Estradiol 17B in Yellow Perch (Perca flavescens), Jeffrey A. Malison, Cody D. Best, Terrance B. Kayes, and Clyde H. Amundson, and Bernard C. Wentworth, 1985, Canadian J. Fish. Aquat. Sci. 42: 1627–1633.

Morrison et al, Organic Chemistry, 4th Ed. pp. 1111–1112 (1983).

Aquaculture, vol. 59, No. 3–4, 1986, Amsterdam, NL pp. 169–175 Gad Degani "Effect of combined dietary 17–beta–estradiol and 17–alpha–. . . ".

Comparative Biochemistry And Physiology, vol. 85A, No. 2, 1986, Oxford, GB pp. 243–247 Gad Degani "Effect of combined dietary 17–beta–estradiol . . . ".

*Primary Examiner*—John W. Rollins
*Assistant Examiner*—Francisco C. Prats
*Attorney, Agent, or Firm*—Wendell R. Guffey

[57] ABSTRACT

A method for promoting growth in fish comprising administering a low level dosage amount of zearalanol to fish. The zearalanol may be conveniently administered to the fish via a novel fish feed formulation comprising a conventional feed mixture supplemented with a relatively low dosage amount of zearalanol ranging from 1 to 20 parts per million (ppm) zearalanol in the feed. In another embodiment, the zearalanol may be administered to the fish in the form of a novel complex of zearalanol and a cyclodextrin compound which further enhances the growth process.

15 Claims, No Drawings

5,593,978

GROWTH PROMOTING COMPOSITION FOR FISH AND METHOD OF USING THE SAME

BACKGROUND OF THE INVENTION

1. Field of the Invention

The present invention relates generally to the field of aquaculture and fish farming, and is more particularly directed to a composition and novel method of using the same to promote accelerated growth and enhanced feed conversion efficiency in fish.

2. Description of the Related Art

The production of marine and freshwater fish for food and other commercial or recreational purposes is a fast growing industry in the United States and throughout the world. In order to meet product demands and to sustain high crop yields, aquaculturists have long strived to develop methods for promoting and enhancing growth in fish. To this end, water quality and disease management techniques have been used and continue to be developed to provide a stress free fish farm environment that is conducive to growth. In addition, nutritional studies have provided insight as to the type and amount of nutrients required by various species of fish to reach their maximum growth potential.

Prompted in part by the noted successes of the animal husbandry industry, aquaculturists have also investigated various methods that are known to stimulate accelerated tissue growth, improve feed conversion efficiency and increase lean to fat ratios in livestock. For example, a positive growth response has been noted when specially prepared polypeptide sequences that stimulate the release of growth hormone (GH) are administered to livestock. Polypeptides have now been developed to similarly stimulate the release of pituitary growth hormone in fish. U.S. Pat. No. 4,843,064 to Vaughan et al. This method has reportedly been useful in accelerating growth in fish, but there are some practical drawbacks to its use in aquaculture. Most notably, GH stimulating polypeptides are generally required to be administered to the fish by parenteral injection or implantation, because digestive enzymes in the digestive tract are expected to cleave and destroy the polypeptide chain if taken orally. Although parenteral application may be feasible for breeding purposes to promote rapid growth of selected stock, it is not generally considered a viable or cost effective method of growth promotion for commercial fishery operations.

Aquaculturists have also investigated the administration of steroids to fish as a method of enhancing growth. Both androgenic and estrogenic compounds have been used extensively and with great success in the animal husbandry industry, however the results in fish have been varied to date. For instance, androgenic compounds, and particularly the androgen methyl-testosterone has generally exhibited a positive growth promoting effect in fish. See, Donaldson, E. M., U. H. M. Fagerlund, D. A. Higgs, and J. R. McBride, 1979. "Hormonal Enhancement of Growth" pp. 455–578. in W. S. Hoar D. J. Randall and J. R. Brett [ed] *Fish Physiology*, Volume 8, Academic Press, New York, N.Y. Yet evidence linking methyltestosterone to cancer has reduced its desirability for use in fish farming, most notably due to concerns regarding the effect that any remaining residue in consumable fish might have on humans. The administration of estrogenic compounds to fish, on the other hand, has rarely shown an enhanced growth effect in fish and has even been linked to inhibiting growth in some species by negatively effecting fish thyroid levels. See, Malison J. A., C. D. Best, T. B. Kayes, C. H. Amundson, and B. C. Wentworth. 1985. "Hormonal Growth Promotion and Evidence for a Size-Related Difference in Response to Estradial-17 in Yellow Perch. (*Perca flavescens*)". Can. J. Fish. Aquat. Sci. 42:1627–1633.

In view of the foregoing, it is a primary object of the present invention to provide a composition for promoting growth in fish that is convenient and cost effective for use in commercial fishery operations.

It is also an object of the present invention to provide a composition and method of use for accelerating the rate of weight gain in fish.

A related object of the present invention is to provide a composition and method of use for increasing the lean to fat ratio in fish.

Another object of the present invention is to provide a growth promoting composition that can be conveniently administered to fish orally.

A further object of the present invention is to provide a composition that is effective in promoting growth in fish when added as a supplement to fish feed.

Another object of the present invention is to provide a feed formulation that effectively promotes accelerated growth in fish.

Yet another object of the present invention is to provide a composition and method of use for promoting growth in juvenile Barramundi fish (*Lares calcerifer*).

It is a further object of the present invention to provide a growth promoting composition and method of using the same that is relatively safe for use with consumable fish.

SUMMARY OF THE INVENTION

These and other objects are achieved by a growth promoting composition for administration to fish, wherein the composition comprises the compound known as zearalanol having the general formula:

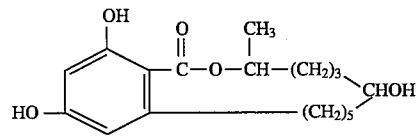

It has been discovered that under otherwise identical conditions, the rate of growth in terms of increased body weight is significantly higher (P<0.05) when the fish diet is supplemented with a low level dose amount of zearalanol. This discovery is particularly surprising because for many years those in the art had concluded that estrogen-like compounds and in particular, zearalanol, were without effect in fish. [See, *Fish Endocrinology*, A. J. Marty (Timber Press, 1985) and Malison, J. A. supra].

In accordance with this invention, the growth promoting zearalanol composition may be admixed with conventional feed components to provide a novel feed formulation. In this manner, the zearalanol composition can be conveniently and safely administered to a relatively large population of fish, such as in commercial fisheries, without the need for costly and burdensome parenteral injection. The growth promotant is provided uniformly on a daily basis to the fish along with their regular diet. Since the fish will consume that amount of feed generally corresponding to their size, the proper amount of zearalanol is consequently provided to each fish, regardless of size variation in the fish population, without the need for individual administration.

Although the growth promoting composition may comprise any form of zearalanol known, in a preferred embodiment of the invention the zearalanol is provided as a novel complex of zearalanol and a cyclodextrin compound. It has been found that this unique complex exhibits a synergistic effect in enhancing growth and feed conversion efficiency in fish when administered as a dietary supplement, such as in a fish feed formulation as heretofore described. In this embodiment, the novel growth promoting complex may be synthesized by mixing an aqueous solution of a cyclodextrin compound with a solvent-based zearalanol solution, and recovering the resultant precipitate comprising the complex.

DETAILED DESCRIPTION OF THE INVENTION

In accordance with the present invention, the resorcyclic acid lactone known as zearalanol[1] and having the formula:

[1] The term zearalanol conforms with the nomenclature in an article in Tetrahedron Letters, Pergamon Press, Ltd., No. 27, pp. 3109–14 (1966).

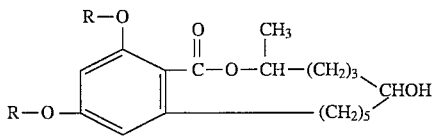

where R is hydrogen or a substituted or unsubstituted alkyl, e.g. lower alkyls such as methyl, ethyl, hexyl, etc. with hydrogen being preferred,
is administered to fish in low level dosage amounts sufficient to promote accelerated body weight growth in the fish. The zearalanol component utilized for purposes of this invention may comprise any commercially available zearalanol composition, or may be prepared according to methods well known in the art.

In general, zearalanol is synthesized by modifying the precursor estrogenic compound zearalenone obtained by cultivating the organism *Gibberella zeae* (Gordon), wherein such modification includes catalytic reduction (i.e. Raney Nickel reduction) of the zearalenone in the presence of hydrogen to yield a mixture of diastereoisomers of zearalanol. This reduction technique is more fully described in U.S. Pat. No. 3,239,345 issued Mar. 8, 1966 to Hodge et al. which is incorporated herein by reference. The racemic mixture of zearalanol so produced may be utilized as the zearalanol component in the present invention without further processing. However, in a preferred embodiment, the zearalanol diamers are separated to provide a zearalanol component comprising at least 50% or more by weight of the higher melting point diamer, the 7α-zearalanol diamer. Most preferably, the zearalanol component will comprise over 85% by weight of 7α-zearalanol which is thought to be more active as a growth promotant. Conventional methods of separating the zearalanol diamers are well known in the art, including those methods described in U.S. Pat. No. 3,239,245 issued Mar. 8, 1966; U.S. Pat. No. 3, U.S. Pat. No. 3,574,235 issued Apr. 6, 1971; and U.S. Pat. No. 3,687,982 issued Aug. 29, 1972 incorporated herein by reference. A suitable source of zearalanol is commercially available in crystallized form from Pitman-Moore, Inc. of Terre Haute, Indiana under the trademark RALGRO®.

The growth promoting composition comprising zearalanol can be administered to the fish by any suitable method known in the art including oral or parenteral administration.

In a preferred embodiment, the zearalanol will be administered to the fish on a daily basis in low level dosage amounts ranging from 3 to 3600 micrograms (μg) zearalanol per kilogram (kg) body weight of the fish (μg/kg), preferably 30 to 1500 μg/kg, with 90 to 180 μg/kg being most preferred. The optimum dosage concentration within these ranges will in part depend upon the species, age and size of the fish being treated, with larger fish generally requiring greater daily amounts of the zearalanol for equivalent results.

Although the growth promoting zearalanol composition may consist of the compound zearalanol by itself, in a preferred embodiment of the invention, the zearalanol is provided as a ligand in a novel complex of zearalanol and a cyclodextrin compound. It has been observed that by administering the zearalanol to fish in the form of a zearalanol-cyclodextrin complex, the overall growth affected by the zearalanol is enhanced. Although the inventors do not wish to be limited by theory, it is hypothesized that by bonding the zearalanol to the cyclodextrin, or to other organic compounds capable of forming a similar complex, complete digestion of the zearalanol by the fish may be enhanced. Furthermore, when comprised in a feed formulation or the like, the bound zearalanol is less likely to prematurely leach out of the formulation when added to the water during feeding, thus assuring complete administration to the fish.

In accordance with this embodiment of the invention, the novel zearalanol-cyclodextrin complex may comprise any cyclodextrin compound capable of forming a complex with zearalanol including alpha-cyclodextrin; gamma-cyclodextrin; hydroxyalkyl cyclodextrins (e.g. hydroxyethyl-beta-cyclodextrin, 2-hydroxypropyl-betacyclodextrin); methyl or dimethylated cyclodextrins (e.g. 2,6-di-O-methyl-beta-cyclodextrin); derivatized alpha, beta and gamma cyclodextrins (e.g. glucosyl-alpha-cyclodextrin or maltosyl-betacyclodextrin); and mixtures thereof; with alpha-cyclodextrin, gamma-cyclodextrin and mixtures thereof being most preferred.

The zearalanol-cyclodextrin complex may be synthesized by any method known in the art, but is preferably prepared by combining an aqueous solution of the cyclodextrin component with a solvent-based solution of zearalanol, and removing the resulting precipitate which comprises the novel complex. Although it should be understood that the relative amounts of the cyclodextrin added to the zearalanol will depend upon the molar ratio of these components in the final complex, these amounts by weight should generally range from 0.5–1.0 to 5.0–1.0 cyclodextrin to zearalanol respectively, with 1.0–3.0 to 3.0–1.0 cyclodextrin to zearalanol being preferred. It is suggested to use a molar excess of the cyclodextrin compound to insure the most efficient utilization of all of the relatively more expensive zearalanol and to minimize the formation of waste streams.

In accordance with the preferred method of preparing the zearalanol-cyclodextrin complex, the cyclodextrin component is dissolved in water in an amount ranging from 1 to 45% by weight cyclodextrin in the total aqueous solution, preferably 2 to 20% cyclodextrin in the total solution and most preferably 4 to 8% by weight of the solution. To enhance the solubility of the cyclodextrin in solution, it is suggested to heat the cyclodextrin solution with agitation to a temperature ranging from 50° to 80° C.

The warm cyclodextrin solution is then added with agitation to a solvent-based zearalanol solution. The zearalanol concentration in the solvent may range generally from 1 to 50% of the total solution, preferably 2 to 25% of the total solution and most preferably 2 to 10% by weight of the total solution. Any compatible water miscible solvent may be used for these purposes including methanol, ethanol, propanol, isopropanol, butanol, 2-butyl alcohol, isobutanol, tertiary butyl alcohol, acetone, methylethyl ketone, dimethyl sulfoxide and dimethylformide. The combined cyclodextrin and zearalanol solutions are then allowed to cool to room temperature over several hours, after which the solid precipitate comprising the complex may be collected by filtration, washing and allowed to dry.

In a preferred embodiment of the present invention, the growth promoting zearalanol composition (whether it be the zearalanol compound alone or the zearalanol-cyclodextrin complex) is incorporated with conventional feed components to provide a novel fish feed formulation for administration to fish. In this manner, the proper amount of zearalanol is administered to each individual fish within a large population of fish often varying in size. The growth promotant is thus easily and conveniently administered to the fish with their regular diet, assuring that the fish receives the desired amount of zearalanol on a continued and daily basis.

The novel feed formulation of the present invention generally comprises a mixture of conventional fish feed components supplemented with a sufficient amount of the zearalanol growth promoting composition to enhance growth in fish. The formulation may be processed in any manner known in the art to provide flakes or pellets that are well suited for fish consumption. Any conventional blend of feed components that is nutritionally balanced for normal fish growth and development can be used for purposes of this invention, taking into consideration the specific nutritional needs of the particular species of fish being cultured. In general, the feed comprises a substantial amount of a protein source preferably ranging from 10% to 70% by weight of the total feed and most preferably in an amount above 35% by weight of the total feed. Suitable sources of protein include soybean meal, fish meal, peanut meal, cottonseed, meat, bone meal or meat meal. The protein component of the feed should include the complete amino acid profile required of the species of fish being cultured or additional amino acids may be added for this purpose.

Carbohydrates are also suggested for addition to the feed as a source of energy and as a filler, preferably in amounts ranging from 1% to 35% by weight of the total feed. Grains and raw fiber such as corn, wheat or grain by-products are good sources of carbohydrates for purposes of the present invention. The feed may also comprise a small amount of fat, such as fish oil, as an additional source of energy preferably in amounts ranging from 1% to 5% by weight of the total feed. Supplemental vitamins, including additional ascorbic acid, minerals and trace elements sufficient to meet the daily nutritional requirements of the fish may be included in the feed as well as other compounds such as anti-microbiles and antibiotics registered for use with fish for consumption.

The zearalanol composition is added to the feed components heretofore described in sufficient amount to promote an accelerated growth response in the fish. The amount of zearalanol compound needed for this purpose generally ranges from about 1 to 20 parts per million (ppm) by weight of the total feed formulation, preferably 2 to 10 ppm and most preferably about 3 to 8 ppm of the total formulation. The formulation will have greatest effect, in terms of promoting growth, if used as a complete fish feed, meaning it is the only significant source of nutrition for the fish. If the feed formulation is instead used in a supplemental manner, generally in cases where fish receive substantial nutrition from environmental sources, the amount of zearalanol in the feed should be increased in a manner to provide the recommended daily dosage amounts of zearalanol as heretofore described.

In preparation of the novel growth promoting feed formulation, the zearalanol growth promoting composition should be thoroughly mixed with the other feed components such that the zearalanol is distributed uniformly throughout the formulation. For best results, it is suggested to combine and mix the zearalanol composition with a portion of one or more of the other ingredients, such as soybean meal or finely ground corn, prior to its being added to the bulk of the other ingredients in the feed mixture.

In a preferred embodiment, the zearalanol composition is first added to a carrier such as corn starch before admixture with the feed components. The use of such a carrier improves the mixability of the zearalanol and also reduces the solubility of the zearalanol component in water such that the zearalanol will not immediately leach into water as soon as the zearalanol containing feed formulation is added to water for feeding. To further improve the water stability and cohesiveness of the fish feed, a binder may be included in the total feed mixture prior to processing. A suitable binder for this purpose includes lignosulphonate.

The novel feed formulation may then be processed by any means now known or later developed in the art, including extrusion or pelleting techniques. Extrusion generally adds an amount of air to the final product, such that the flakes prepared by extrusion usually float when added to water. Pelleting, on the other hand, generally provides a dense pellet that sinks upon addition to water. The desired form of the final feed formulation will depend upon the species and feeding habits of the fish being cultivated.

It is preferred that the final processed feed have a moisture content ranging from 1 to 20% and preferably 3 to 12% by weight of the total feed to assure proper cohesion of the feed components. In general, the feed ingredients may have a sufficient natural moisture content to meet this objective, however additional water may be added to the feed mixture prior to processing if needed. In such event and according to conventional techniques, any excess moisture may then be removed from the processed feed by drying or other means.

Other additives or adjuvants may also be added to the final processed feed as a coating where desired. For instance, it is known to coat processed feed pellets with an amount of oil or fat to enhance the water stability and cohesion of the pellets.

The fish may be fed one or more times per day to satiation by manually broadcasting the novel zearalanol supplemented feed formulation across the surface of the water or automatically from mechanical feeders. In order to achieve maximum growth in accordance with this invention, the daily nutrient requirements of the fish must be met. In addition, disease and water quality management techniques should be utilized to provide a healthy and stress free environment for normal growth and development.

Modifications and variations of the present invention, diet compositions and methods for formulation and administration thereof to fish will be obvious to those skilled in the art from the foregoing detailed description. Such modifications and variations are intended to come within the scope of the amended claims.

The following examples are offered to illustrate important aspects of the present invention; however, the invention is not limited to the specific materials, amounts, and procedures set forth below or to the specific species and age of fish utilized.

EXAMPLE I

PREPARATION OF ZEARALANOL-CYCLODEXTRIN COMPLEX

An aqueous cyclodextrin solution was prepared by adding about 5 to 20 grams (g) beta-cyclodextrin to 40 to 100 milliliters (mL) of water and heating the solution to about 50°–80° C. with agitation. A solvent based zearalanol solution was prepared by dissolving about 1 to 5 g of zearalanol[2] in about 10 to 50 mL of a water miscible solvent such as methanol.

[2] 6-(6,10-Dihydroxyundecyl)-β-resorcyclic acid-μ-lactone, available from Pitman-Moore, Inc., Terre Haute, Ind. under the trademark RALGRO®. The solvent based zearalanol solution was then added with agitation to the warm cyctodextrin solution, and the solution was cooled to room temperature over several hours time. The solid precipitate formed was collected by filtration washing with a limited quantity of water and allowed to air dry providing a free flowing zearalanol-cyclodextrin solid.

Formation of the zearalanol-cyclodextrin complex was confirmed via differential scanning calorimetry (DSC) indicating that the zearalanol was incorporated within an occlusion or cavity of a host cyclodextrin molecule.

EXAMPLE II

PREPARATION OF CONTROL AND ZEARALANOL DOSED FEED FORMULATIONS

A conventional fish feed mixture or basil diet premix meeting the nutrient requirements of juvenile Barramundi fish was prepared as follows:

TABLE I

| BASIL DIET INGREDIENTS | % BY WEIGHT DRY MATTER (Total Basil Diet) |
|---|---|
| Wheat | 25 |
| Fish meal | 55 |
| Soybean meal | 10 |
| Fish oil | 3 |
| Vitamin premix | 2 |
| Corn starch | 5 |

A zearalanol supplemented feed formulation was prepared by thoroughly mixing zearalanol[3] to the corn starch prior to mixing with the other basal ingredients and pelleting. Zearalanol was included at 100 mg per/kg of corn starch. The resulting zearalanol premix was then added to the other basil diet ingredients in an amount of about 5% weight of the total mixture to provide a feed dosed with about 5 ppm zearalanol.

A zearalanol-cyclodextrin supplemented feed formulation was also prepared by first mixing about 500 mg of the zearalanol-cyclodextrin complex synthesized in Example I with about 1 kg of corn starch. The resulting zearalanol-cyclodextrin premix was then added to the other basil diet ingredients in an amount of about 5% by weight of the total mixture to provide a feed dosed with about 5 ppm zearalanol.

The feed mixtures were then compressed by a benchtop pellet machine to form four millimeter by two millimeter pellets. The total moisture content of the pellets was about 8% by weight of the total pellet. The pellets were stored separately in sealed drums in an air conditioned room at approximately 20° C.

[3] 6-(6,10-Dihydroxyundecyl)-β-resorcyclic acid-μ-lactone, available from Pitman-Moore, Inc., Terre Haute, Ind. under the trademark RALGRO®.

EXAMPLE III

EFFECT OF ZEARALANOL ON TOTAL BODY WEIGHT GROWTH IN FISH

In this example, juvenile Barramundi fish (*Lates calcarifer*) are presented in environmental conditions suitable for their life and growth. The effect of the zearalanol supplemented feeds as prepared in Example II above on total body weight growth of the fish was examined.

EXPERIMENTAL 150 juvenile Barramundi fish were randomly allotted to six treatment groups of 25 fish each, whereby the average mean weight of each group at week O was approximately 74 grams (g). Each group was maintained in a cage (400 millimeters (mm) long×400 mm wide×400 mm deep), wherein all six cages were placed within the same community tank (36 L/min flow rate). Optimum water temperature and water quality conditions for growth of the Barramundi were maintained throughout the experimental period.

The fish were fed one of three diets during the experimental period. Two groups were fed the basil diet premix in pelleted form containing no zearalanol additive as the controls. Two groups were fed the zearalanol supplemented pellets and the remaining two groups were fed the zearalanol-cyclodextrin complex supplemented pellets. The fish were fed once daily to satiation. The treatment phase lasted three weeks. Weight measurements on the individual fish were taken at weeks O, 1, 2 and 3.

RESULTS a) The mean fish weight ($\bar{x}$) of the fish in each compartment was calculated from the formula:

$$\bar{x} = \sum_{i=1}^{n} x_i/n$$

where $X_i$ is the weight of the ith fish in the compartment and n is the number of fish in the compartment.

These were calculated for weeks 0, 1, 2 and 3 as shown below:

TABLE II

Effect of Zearalanol on the Mean Weight (g) of juvenile Barramundi

| Time (week) | Treatment | | |
|---|---|---|---|
| | control | zearalanol | zearalanol-cyclodextrin |
| 0 | 74.0 | 74.2 | 72.5 |
| 1 | 92.5 | 93.3 | 94.0 |
| 2 | 113.8 | 114.5 | 115.5 |
| 3 | 143.7 | 147.2 | 145.5 | b) The weight gain of the fish per compartment was calculated by subtracting the first date from the final (fourth) date. Relative to the control group, there was a 4.6% and 4.9% increase in the overall liveweight of the zearalanol and zearalanol-cyclodextrin groups respectively.

c) The linear relationship between the fish weights and time was calculated using the linear regression line. This is the line which 'best fits' the observed measurements.

The line is $W=A+BT$ where W is the fish weight and T is the time. B is calculated from the formula $$B = \sum_{i=1}^{4} (W_i - \overline{w})(T_i - \overline{t}) / \sum_{i=1}^{4} (T_i - \overline{t})^2$$

where $W_i$=the average fish weight at time i,
$T_i$=the time (i.e. 1, 2, 3, 4)
$\overline{w}$=the average weight over all 4 times,
$\overline{t}$=the average time over all 4 times,
A is calculated from the formula:

$$A = \overline{w} - B\overline{t}$$

These regression lines were calculated for each compartment. The regression coefficients give the growth rates. Relative to the control group, the zearalanol supplemented group produced a 4.4% growth rate improvement ($p<0.1$), and the zearalanol-cyclodextrin group improved growth rate by 4.8% ($p<0.05$). The combined mean growth rate of both zearalanol groups was significantly greater ($p<0.05$) than the control group.

What is claimed is:

1. A growth promoting composition useful for promoting growth in fish comprising a complex of zearalanol and a cyclodextrin compound.

2. A composition according to claim 1, wherein said zearalanol comprises the compound having the formula:

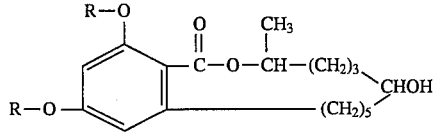

where R is hydrogen or an unsubstituted $C_1$–$C_6$ alkyl.

3. A composition in accordance with claim 1, wherein said cyclodextrin compound is selected from the group consisting of alpha-cyclodextrin, gamma-cyclodextrin, hydroxyalkyl-cyclodextrins, methyl or dimethylated cyclodextrins, derivatized alpha, beta and gamma cyclodextrins, and mixtures thereof.

4. A composition in accordance with claim 3, wherein said cyclodextrin is selected from the group consisting of alpha-cyclodextrin, gamma-cyclodextrin and mixtures thereof.

5. A composition according to claim 2, wherein R is hydrogen.

6. A feed composition useful for promoting growth in fish comprising a mixture of fish feed and a zearalanol component bound to a cyclodextrin compound to form a zearalanol-cyclodextrin complex, wherein the zearalanol component is provided in an amount sufficient to promote accelerated growth in the fish, said amount ranging from about 1 to about 20 parts per million (ppm) by weight of the total composition.

7. A composition according to claim 6, wherein said feed includes the daily nutrient requirements of said fish.

8. A composition according to claim 6, wherein said zearalanol component comprises the zearalanol compound having the formula:

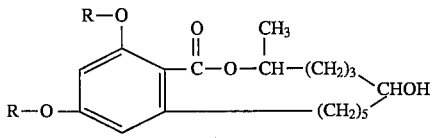

where R is hydrogen or an unsubstituted $C_1$–$C_6$ alkyl.

9. A composition according to claim 8, wherein R is hydrogen.

10. A composition according to claim 8, wherein said zearalanol is present in said composition in an amount ranging from 3 to 8 ppm of the total composition.

11. A composition according to claim 8, wherein said composition is the primary source of nutrition for said fish.

12. A composition according to claim 6, wherein said composition additionally includes a binder.

13. A composition according to claim 6, wherein said composition is in the form of pellets.

14. A composition according to claim 6, wherein said composition is in extruded form.

15. A composition according to claim 6, wherein said zearalanol component is uniformly mixed with said feed.

* * * * *